United States Patent [19]

Amino et al.

[11] Patent Number: 5,106,962

[45] Date of Patent: Apr. 21, 1992

[54] PROCESS FOR PREPARING 2′,3′-DIDEOXY NUCLEOSIDE DERIVATIVES

[75] Inventors: Yusuke Amino; Hisao Iwagami, both of Kawasaki, Japan

[73] Assignee: Ajinomoto Co., Inc., Tokyo, Japan

[21] Appl. No.: 525,030

[22] Filed: May 18, 1990

[30] Foreign Application Priority Data

May 26, 1989 [JP] Japan .................................. 1-134186

[51] Int. Cl.$^5$ .................. C07H 19/473; C07H 19/167
[52] U.S. Cl. ........................................ 536/23; 536/24; 536/26
[58] Field of Search ........................ 536/22, 23, 24, 26

[56] References Cited

U.S. PATENT DOCUMENTS 3,280,104 10/1966 Moffatt et al. ...................... 536/28

OTHER PUBLICATIONS

Kim-Thuan et al., Journal of Photochemistry, vol. 13, 257–259 (1980).
White et al., European J. Biochem., vol. 184, 89–96 (1989).

Primary Examiner—Johnnie R. Brown
Assistant Examiner—L. Eric Crane
Attorney, Agent, or Firm—Oblon, Spivak, McClelland, Maier & Neustadt

[57] ABSTRACT

A process for preparing 2′,3′-didehydro-2′,3′-dideoxynucleoside derivatives (III)

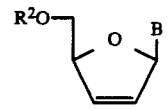

by reacting a compound (I)

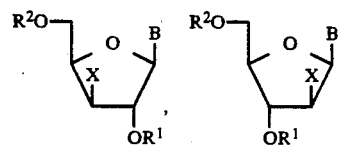

or

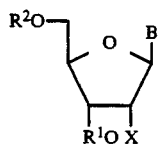

with a viologen (N,N′-dialkyl-4,4′-bipyridinium salt) is disclosed. In the formulae $R^1$ is $C_{1-12}$ acyl or sulfonyl, $R^2$ is hydrogen, $C_{1-12}$ acyl, $C_{1-12}$ alkyl, $C_{6-18}$ aralkyl, or silyl, X is a halogen atom, and B is a purine, pyrimidine, imidazole, or triazole base residue.

8 Claims, No Drawings

PROCESS FOR PREPARING 2',3'-DIDEOXY NUCLEOSIDE DERIVATIVES

BACKGROUND OF THE INVENTION

1. Field of the Invention

The present invention generally relates to processes for transforming 1,2-diols into olefins, and more particularly to processes for preparing nucleoside derivatives.

2. Discussion of the Background

To convert compounds of formula (I)

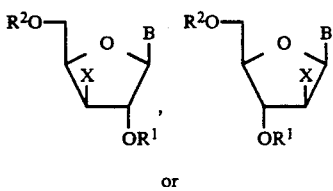

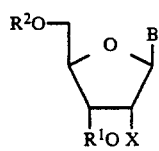

into the 2',3'-didehydro-2',3'-dideoxynucleoside derivatives of formula (III)

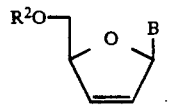

which are important intermediates for preparing pharmaceutically active substances such as antiviral agents, the following known methods can be used:

(1) a method using Zn—AcOH (M. J. Robins et al., Tetrahedron Lett., 25, 367 (1984); B. Samuelsson et al., Acta Chem. Scand., B36, 215 (1982); J. Chattopadhyaya et al., Acta Chem. Scand., B40, 251 (1982));

(2) a method using Cr(OAc)$_2$en$_2$ (T. C. Jain et al., J. Org. Chem., 39, 30 (1974));

(3) a method using electrode mediated reduction (T. Adachi et al., J. Org. Chem., 44, 1404 (1979)); etc.

With method (1), it is difficult to remove the zinc complexes from the reaction mixture. With method (2) it is difficult to prepare the reactants used and several by-products are formed due to the difficult separation operations used therein. Method (3) suffers the problem that a special reaction device is required.

There is thus a need for a better process for preparing the compounds of formula (III) from compounds of formula (I).

SUMMARY OF THE INVENTION

Accordingly it is an object of the present invention to provide a process for highly selectively producing 2',3'-didehydro-2',3'-dideoxynucleoside derivatives of formula (III) from compounds of formula (I) in a simple manner, which process does not require any complicated reaction apparatuses or synthetic steps.

The present inventors have found that these objects, and other objects which will become apparent from the description of the invention given hereinbelow, are satisfied with a process in which 2',3'-didehydro-2',3'-dideoxynucleoside derivatives of formula (III)

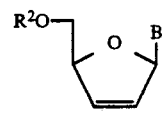

can be readily obtained from nucleosides in that they are highly selectively prepared in a high yield by reacting compounds of formula (I)

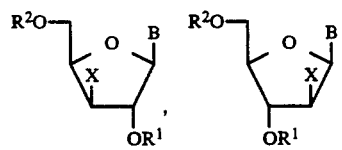

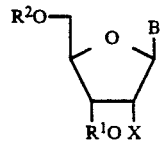

with viologen (N,N'-dialkyl-4,4'-bipyridinium salts), compounds of the formula (II)

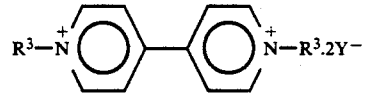

in an appropriate solvent in the presence of a base under electron-donating reaction conditions. With this purpose only the by-products

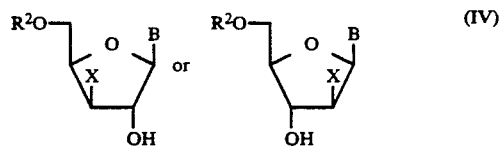

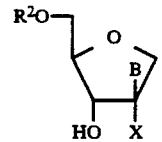

are formed.

DETAILED DESCRIPTION OF PREFERRED EMBODIMENTS

The present invention thus relates to 2',3'-didehydro-2',3'-dideoxynucleoside derivatives which are intermediates for synthesis of 2',3'-dideoxynucleosides useful as drugs such as antiviral agents, etc. and to a novel process for preparing 2',3'-didehydro-2',3'-dideoxynucleoside derivatives using the intermediates.

In the above formulae,

R$^1$ is a C$_{1-12}$ acyl group or a sulfonyl group;

R$^2$ is a hydrogen atom, a C$_{1-12}$ acyl group, a C$_{1-12}$ alkyl group, a C$_{6-18}$ aralkyl group, or a silyl group;

R$^3$ is a C$_{1-20}$ alkyl group, or a C$_{6-20}$ aralkyl group;

X and Y, which may be the same or different, each is a halogen atom;

B is a purine base bound at its 1-position, a pyrimidine base bound at its 1-position, an imidazole base bound at its 1-position, or a triazole base bound at its 1-position, to the sugar residue.

Examples of the $R^1$ acyl groups include acetyl, propionyl, benzoyl, etc. Examples of the sulfonyl group include tosyl, mesyl, etc.

Examples of the $R^2$ acyl groups include acetyl, propionyl, benzoyl, etc.; examples of the $R^2$ alkyl groups include methyl, ethyl, etc.; examples of the $R^2$ aralkyl groups include benzyl, phenylethyl, phenylpropyl, etc.; examples of the $R^2$ silyl groups include t-butyldimethylsilyl, and the like.

Examples of the $R^3$ alkyl groups include methyl, propyl, heptyl, octyl, dodecyl, etc.; and examples of the $R^3$ aralkyl groups include benzyl, phenylethyl, phenylpropyl etc.

For X and Y the preferred halogen atoms are chlorine, bromine or iodine.

For variable B, examples of the purine base include adenine, quanine, hypoxanthine, xanthine, 6-chloropurine, 6-mercaptopurine, 6-methylthiopurine, 2,6-dichloropurine, 2-chloropurine, 2,6-diaminopurine, 2-amino-6-chloropurine, 2-aminopurine, etc.; examples of the pyridine base include uracil, cytosine, thymine, 5-fluorouracil, 5-chlorouracil, 5-iodouracil, 5-ethyluracil, orothic acid, etc.; examples of the imidazole base include 5-amino-4-imidazolecarboxamide, etc.; and examples of the triazole base include 1,2,4-triazole-3-carboxamide, etc. If necessary, amino groups, etc. in the nucleotide moiety may be protected.

The compounds of formula (I) can be prepared from nucleosides in a conventional manner (cf., *J. Am. Chem. Soc., 95, 4025* (1973)). The compounds of formula (II) may also be synthesized according to a known process (cf., *J. Am. Chem. Soc., 106, 6217* (1984)).

It is known that the compounds of formula (II) accept electrons from suitable compounds to become cation radicals, and that the radicals act as electron donors for other compounds. There are examples of the reduction of aldehydes, ketones, keto esters, azobenzene, vicinal dihalides, nitroalkanes, etc. using this approach. But the present invention provides, for the first time, the use of these compounds to reduce a vicinal haloacyl (e.g., bromoacetate) compounds to obtain a corresponding olefin.

As the solvent, it is preferred to use a two phase-type solvent system comprised of an organic solvent and water. As the organic solvent, methylene chloride, ethyl acetate, acetonitrile, etc. can be used.

Specific examples of results obtained in reactions using various organic solvents are shown in Table I.

When 9-(2,5-di-O-acetyl-3-bromo-3-deoxy-β-D-xylofuranosyl) adenine is reacted with 0.5 molar amount of heptylviologen (N,N'-diheptyl-4,4'-bipyridinium dibromide; hereafter abbreviated as $C_7V$) in a solvent mixture of an organic solvent and water (7:3(v/v)), 5'-O-acetyl-2',3'-didehydro-2',3'-dideoxynucleoside is obtained as the product. The results were analyzed by HPLC.

As the bases, 6 molar equivalents of $K_2CO_3$ and 10 molar equivalents of $Na_2S_2O_4$ were used and the reaction was carried out at room temperature for 15 hours in an argon atmosphere.

As shown in Table I, some organic solvents are effective. But from a point of view of low by-products production, etc., methylene chloride and then ethyl acetate were excellent.

TABLE I $$AB.Ar^{1)} \xrightarrow{C_7V^{2)} (0.5 \text{ eq})}{\text{organic solvent-water}} AcDH.DDA^{3)}$$

| Organic Solvent | Conversion Rate[4] (%) | AcDH.DDA[4] (%) | By-Product[4],[5] (%) |
|---|---|---|---|
| $CH_2Cl_2$ | 75 | 69 | 4 |
| AcDEt | 74 | 56 | 16 |
| $CH_3CN$ | 28 | 3 | 23 |
| $CH_3OH$ | 100[6] | trace | trace |

Reaction conditions: in an argon atmosphere, organic solvent-water (7:3, v/v, 24 mM), $C_7V$ (0.5 eq), $Na_2S_2O_4$ (10 eq), $K_2CO_3$ (6 eq), room temperature; agitation for 15 hours.
[1] 9-(2,5-di-O-acetyl-3-bromo-3-deoxy-β-D-xylofuranosyl)-adenine
[2] N,N'-diheptyl-4,4'-bipyridinium dibromide
[3] 5'-O-acetyl-2',3'-didehydro-2',3'-dideoxyadenosine
[4] calculated from an area ratio by HPLC
Conditions for HPLC: column, YMC-Pack A-312 ODS (6 φ mm × 150 mm); eluent, 20% acetonitrile; flow rate, 1.6 ml/min; detection wavelength at 260 nm
[5] 9-(5-O-acetyl-3-bromo-3-deoxy-β-D-xylofuranosyl)-adenine
[6] Hydrolysis proceeds.

As the base, inorganic salts such as $K_2CO_3$, $Na_2S_2O_4$, etc. or organic bases such as triethylamine, etc. are used. It is desired to use 2 to 10 molar equivalents of the base based on the amount of substrate used.

As the electron donor, it is advantageous to use $Na_2S_2C_4$ from a point of view of economic and operational considerations. It is desired to use 2 to 10 molar equivalents of $Na_2S_2O_4$ based on the amount of substrate used. Using $Na_2EDTA$-$Ru(bpy)^{2+}$ instead of $Na_2S_2C_4$ followed by exposure to light, or using a palladium-carbon catalyst and a hydrogen atmosphere are also possible.

To examine the ability of compounds of formula (II) to act as catalysts, $C_7V$ was reacted with 9-(2,5-di-O-acetyl-3-bromo-3-deoxy-β-D-xylofuranosyl)adenine in various molar ratios followed by analysis with HPLC. The results are shown in Table II.

The reaction conditions are the same as in Table I except that the molar ratio of $C_7V$ is varied in a $CH_2Cl_2$-water solvent system (7:3(v/v)).

In Table II, as is understood from the results in the reaction using 0.1 molar equivalent and 0.5 molar equivalent $C_7V$, the reaction proceeds catalytically. However, under the reaction conditions used, more than one molar equivalent of $C_7V$ was required to complete the reaction.

TABLE II $$AB.AR \xrightarrow{C_7V \ (\times \ eq)} AcDH.DDA$$

| Molar Equivalent of $C_7V$ | Conversion Rate (%) | AcDH.DDA (%) | By-Product (%) |
|---|---|---|---|
| 0.1 | 40 | 35 | 4 |
| 0.5 | 75 | 69 | 4 |
| 1.0 | 96 | 92 | 3 |
| 1.5 | 99 | 94 | 4 |

Reaction conditions: in an argon atmosphere, $CH_2Cl_2$-water (7:3, v/v, 24 mM), $Na_2S_2O_4$ (10 eq), $K_2CO_3$ (6 eq), room temperature; agitation for 15 hours.

To examine the effect of substituent $R^3$ of the compounds of formula (II), various compounds of formula (II) were reacted with 9-(2,5-di-O-acetyl-3-bromo-3-deoxy-β-D-xylo-furanosyl) adenine. The results obtained are shown in Table III.

The reaction was carried out in a solvent system of $CH_2Cl_2$-water (7:3(v/v)) in an argon atmosphere. After 0.5 molar equivalent of a compound of formula (II) was stirred in the presence of 10 molar equivalents of $Na_2S$-

$_2O_4$ and 6 molar equivalents of $K_2CO_3$ for 15 hours, 0.2 to 0.3 molar equivalents of (II), 2 molar equivalents of $Na_2S_2O_4$ and 2 molar equivalents of $K_2CO_3$ were further supplemented. The reaction was continued for 24 hours. The produced 5'-O-acetyl-2',3'-didehydro-2',3'-dideoxynucleoside was purified by HPLC and its yield was determined.

As is shown in Table III, the results reveal that the compounds of formula (II) having as $R^3$ methyl ($C_1V$), propyl ($C_3V$), octyl ($C_8V$) and dodecyl ($C_{12}V$) all gave the desired 5'-O-acetyl-2',3'-didehydro-2',3'-dideoxynucleoside in high selectivity and high yield, as in $C_7V$.

TABLE III $$AB.AR \xrightarrow{CxV^{1)}} AcDH.DDA$$

| CxV (II) | Conversion Rate (%) | Yield,[2] (%) | By-Product (%) |
|---|---|---|---|
| $C_1V$ | 86 | 75 | 1 |
| $C_3V$ | 94 | 79 | 2 |
| $C_8V$ | 93 | 72 | 7 |
| $C_{12}V$ | 92 | 74 | 4 |

Reaction conditions: in an argon atmosphere, $CH_2Cl_2$-water (7:3, v/v, 24 mM), CxV (0.5 eq), $Na_2S_2O_4$ (10 eq), $K_2CO_3$ (6 eq), room temperature; agitation for 15 hours; then, CxV (0.2 to 0.3 eq) is added followed by stirring at room temperature for 24 hours.
[1] $C_1V$ (N,N'-dimethyl-4,4'-bipyridinium dichloride), $C_3V$ (N,N'-dipropyl-4,4'-bipyridinium dichloride), $C_8V$ (N,N'-dioctyl-4,4'-bipyridinium dichloride) and $C_{12}V$ (N,N'-didodecyl-4,4'-bipyridinium dichloride)
[2] Yield after isolation The reaction was also applied to various nucleoside derivatives. The results are shown in Table IV.

The reaction conditions were identical to those in Table III but, in addition to 9-(2,5-di-O-acetyl-3-bromo-3-deoxy-β-D-xylofuranosyl)adenine, a mixture of 9-(2,5-di-O-acetyl-3-bromo-3-deoxy-β-D-xylofuranosyl)-hypoxanthine and 9-(3,5-di-O-acetyl-2-bromo-2-deoxy-β-D-xylofuranosyl)hypoxanthine, and 3',5'-O-diacetyl-2'-bromo-2-deoxyuridine were used as substrates to give 5'-O-acetyl-2',3'-didehydro-2',3'-dideoxyadenosine, 5'-O-acetyl-2',3'-didehydro-2',3'-dideoxyinosine and 5'-O-acetyl-2',3'-didehydro-2',3'-dideoxyuridine.

It was observed that the reaction proceeded irrespective of kind of nucleic acid bases and kind of isomers at the 2',3'-positions.

TABLE IV $$AB.AR^{1)} \xrightarrow{C_7V} AcDH.DDX^{2)}$$

| Substrate | Product | Conversion Rate (%) | Yield (%) | By-Product (%) |
|---|---|---|---|---|
| AB.AR | AcDH.DDA | 94 | 83 | 3 |
| AB.HxR | AcDH.DDI | 96 | 78 | 3[3] |
| AB.UR | AcDH.DDU | 90 | 64 | 4[4] |

Reaction conditions: same as in Table III
[1] AB.HxR: 9-(2(3),5-di-O-acetyl-3(2)-bromo-3(2)-deoxy-β-D-xylofuranosyl)hypoxanthine, AB.UR: 3',5'-di-O-acetyl-2'-bromo-2'-deoxyuridine
[2] AcDH.DDI: 5'-O-acetyl-2',3'-didehydro-2',3'-dideoxyinosine, AcDH.DDV: 5'-O-acetyl-2',3'-didehydro-2',3'-dideoxyuridine
[3] 5-(5-O-acetyl-3(2)-bromo-3(2)-deoxy-β-D-xylo-furanosyl)hypoxanthine
[4] 5'-O-acetyl-2'-bromo-2'-deoxyuridine The thus obtained 5'-O-acetyl-2',3'-didehydry-2',3'-dideoxynucleosides can be converted into 5'-O-acetyl-2',3'-dideoxynucleosides by catalytic hydrogenation using a palladium catalyst, etc.

The 2',3'-didehydro-2',3'-dideoxynucleoside derivatives prepared by the foregoing process can be subjected to a reducing step in a conventional manner to give 2',3'-dideoxynucleoside derivatives. For example, the reducing step can include reduction by catalytic hydrogenation in the presence of a palladium catalyst.

As described hereinabove, according to the present invention, 2', 3'-didehydro-2',3'-dideoxynucleoside derivatives which are important intermediates for preparing pharmacologically active substances can be obtained in a high purity and high yield. The present invention can also be used Mutatis, Mutandis, as a general method for the conversion of 1,2-diols into olefins.

Having generally described this invention, a further understanding can be obtained by reference to certain specific examples which are provided herein for purposes of illustration only and are not intended to be limiting unless otherwise specified.

EXAMPLE 1

Preparation of 5'-O-acetyl-2',3'-didehydro-2',3'-dideoxyadenosine)

To a solvent mixture of 35 ml of methylene chloride and 15 ml of water were added 500 mg (1.21 mmol) of 9-(2,5-di-O-acetyl-3-bromo-3-deoxy-β-D-xylofuranosyl)adenine, 2.09 g (12.0 mmols) of $Na_2S_2O_4$ and 995 mg (7.2 mmols) of $K_2CO_3$. The mixture was stirred for a while in an argon atmosphere. Then 308 mg (0.6 mmol) of N,N'-diheptyl-4,4'-bipyridinium dibromide was added and the mixture was stirred at 28° C. for 15 hours. Furthermore, 418 mg of $Na_2S_2C_4$, 380 mg of $K_2CO_3$ and 185 mg (0.36 mmol) of N,N'-diheptyl-4,4'-bipyridinium dibromide were supplemented followed by stirring for 24 hours. To the mixture was added 50 ml of methylene chloride. The mixture was fractionated and the organic phase was dried over anhydrous magnesium sulfate. After filtering and concentration, the concentrate was purified by silica gel PTLC [Whatman PLK-5F, developed with ethyl acetate-methanol (8:1)] to give 276 mg (83%) of 5'-O-acetyl-2',3'-didehydro-2',3'-dideoxyadenosine.

EXAMPLE 2

Preparation of 5'-O-acetyl-2',3'-didehydro-2',3'-dideoxyionsine

The reaction was carried out in a manner similar to Example 1 except that 475 mg (1.14 mmol) of a mixture of 9-(2,5-di-O-acetyl-3-bromo-3-deoxy-β-D-xylofuranosyl)hypoxanthine and 9-(3,5-di-O-acetyl-2-bromo-2-deoxy-β-D-xylofuranosyl)hypoxanthine was used. Thus, 246 mg (78%) of 5'-O-acetyl-2',3'-didehydro-2',3'-dideoxyinosine.

EXAMPLE 3

Preparation of 5'-O-acetyl-2',3'-didehydro-2',3'-dideoxyuridine

The reaction was carried out in a manner similar to Example 1 except that 450 mg (1.15 mmol) of 3',5'-di-O-acetyl-2'-bromo-2'-deoxy-uridine was used. Thus, 183 mg (64%) of 5'-O-acetyl-2',3'-didehydro-2',3'-dideoxyuridine.

EXAMPLE 4

Preparation of 5'-O-acetyl-2',3'-dideoxyadenosine

To 120 ml of acetonitrile were added 1.50 g (3.62 mmols) of 9-(2,5-di-O-acetyl-3-bromo-3-deoxy-β-D-xylofuranosyl) adenine, 946 mg (1.84 mmol) of N,N'-diheptyl-4,4'-bipyridinium dibromide, 1.13 g of 10% palladium-carbon (water content, 50%) and 2.5 ml of triethylamine. The mixture was stirred for 2 hours at room temperature in a hydrogen atmosphere. The analysis by HPLC reveals that the raw material disappeared and 5'-O-acetyl-2',3'-didehydro-2',3'-dideoxyadenosine (85), 5'-O-acetyl-2',3'-dideoxyadenosine (11%) and 2',5'-di-O-acetyl-3'-deoxyadenosine (3%) were formed.

After 0.5 g of 10% palladium-carbon was added to the reaction solution, the mixture was stirred for 6 hours in a hydrogen atmosphere.

The catalyst was removed by filtration. After the filtrate was concentrated under reduced pressure, the concentrate was purified by silica gel PTLC to give 0.69 g (69%) of 5'-O-acetyl-2',3'-dideoxyadenosine.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for preparing a 2',3'-didehydro-2',3'-dideoxynucleoside derivative of formula (III):

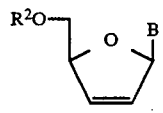

which process comprises:
(i) reacting a compound of formula (I):

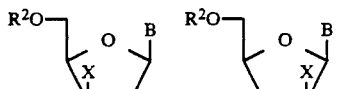

or

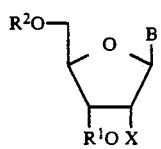

with a viologen (N,N'-dialkyl-4,4'-bipyridinium salt) compound of formula (II):

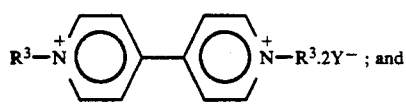

(ii) obtaining said compound of formula (III): wherein
$R^1$ is a $C_{1-12}$ acyl group or a sulfonyl group;
$R^2$ is a hydrogen atom, a $C_{1-12}$ acyl group, a $C_{1-12}$ alkyl group, $C_{6-18}$ aralkyl group, or silyl group;
$R^3$ is a $C_{1-20}$ alkyl group of $C_{6-20}$ aralkyl group;
X and Y are each independently a halogen atom;
B is a purine base bound at its 9-position or a pyrimidine base bound at its 1-position, to the 1'-position of the sugar residue.

2. The process of claim 1, wherein either (a) $Na_2S_2O_4$ or (b) a palladium-carbon catalyst and a hydrogen atmosphere are used in step (i).

3. The process of claim 2, wherein a solvent system comprised of a mixture of an organic solvent and water is used.

4. The process of claim 3, wherein said organic solvent is methylene chloride, ethyl acetate or acetonitrile.

5. The process of claim 3, wherein a carbonate, an acetate, or an organic base is used as a base in step (i).

6. The process of claim 5, wherein potassium carbonate or sodium carbonate is used as said base.

7. The process of claim 1, wherein a palladium-carbon, Pd-BaCO₃ or Pd-BaSO₄ catalyst is used in step (i) in the presence of a hydrogen atmosphere.

8. A process for the one pot synthesis of a 2',3'-dideoxynucleoside derivative, comprising:
(i) preparing a 2',3'-didehydro-2',3'-dideoxynucleoside derivative of formula (III)

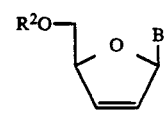

by (ia) reacting a compound of formula (I):

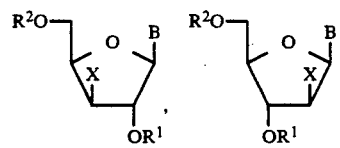

or

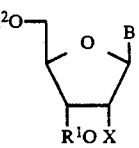

with a viologen (N,N'-dialkyl-4,4'-bipyridinium salt) compound of formula (II):

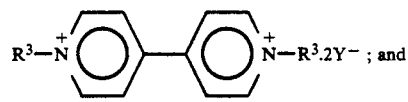

(ib) obtaining said compound of formula (III): wherein
$R^1$ is a $C_{1-12}$ acyl group or a sulfonyl group;
$R^2$ is a hydrogen atom, a $C_{1-12}$ acyl group, a $C_{1-12}$ alkyl group, a $C_{6-18}$ aralkyl group, or silyl group;
$R^3$ is a $C_{1-20}$ alkyl group or $C_{6-20}$ aralkyl group;
X and Y are each independently a halogen atom;
B is a purine base bound at its 9-position or a pyrimidine base bound at its 1-position, to the 1'-position of the sugar residue; and
(ii) subjecting, in the same pot, said 2',3'-didehydro-2',3'-dideoxynucleoside derivative of formula (III) to a reduction step to obtain said 2',3'-dideoxynucleoside derivative.

* * * * *